United States Patent [19]

Heady

[11] 4,317,880

[45] Mar. 2, 1982

[54] PROCESS FOR THE PRODUCTION OF FRUCTOSE POLYMERS AND HIGH FRUCTOSE SYRUPS

[75] Inventor: Robert E. Heady, Park Forest, Ill.

[73] Assignee: CPC International Inc., Englewood Cliffs, N.J.

[21] Appl. No.: 156,154

[22] Filed: Jun. 3, 1980

[51] Int. Cl.³ .................... C12P 19/02; C12P 19/18; C12P 19/24

[52] U.S. Cl. .................... 435/94; 435/97; 435/105; 435/813; 435/911

[58] Field of Search ............... 435/94, 97, 101, 105, 435/813, 911

[56] References Cited

U.S. PATENT DOCUMENTS 4,077,842  3/1978  Cory .................... 435/188

FOREIGN PATENT DOCUMENTS 2000144  1/1979  United Kingdom .

*Primary Examiner*—Esther M. Kepplinger
*Attorney, Agent, or Firm*—Stanley M. Parmerter

[57] ABSTRACT

This invention relates to a process especially useful for the preparation of novel fructose polymers and high fructose syrups from sucrose.

12 Claims, No Drawings

PROCESS FOR THE PRODUCTION OF FRUCTOSE POLYMERS AND HIGH FRUCTOSE SYRUPS

FIELD OF THE INVENTION

This invention relates to a process for the production of fructose polymers from sucrose. The fructose polymers produced can easily be converted to syrups of high fructose content.

BACKGROUND OF THE INVENTION

Commercial fructose-containing syrups are manufactured by the enzymatic isomerization of glucose obtained from corn-derived starch hydrolyzates. This is usually accomplished in a continuous process which involves contacting the glucose-containing solution with a glucose isomerase enzyme preparation that has been immobilized in some fashion. These procedures give a syrup in which fructose is less than 50%, usually 40-45%, of the total carbohydrate present.

Because fructose is sweeter than either glucose or sucrose, much effort has gone into developing processes for producing syrups in which more than 50% of the carbohydrate is fructose. Typically, these methods have involved chromatographic procedures for separating the fructose from the other carbohydrates contained in syrups derived from sucrose and/or corn. Examples are U.S. Pat. Nos. 4,096,036, 4,022,637 and 3,483,031.

Recently, a novel way to obtain fructose syrup of greater than 50% fructose content was disclosed in British patent specification No. 2,000,144. According to that procedure, a sucrose substrate is subjected to the action of a fructosyl transferase enzyme to convert the sucrose to an intermediate syrup containing predominantly fructose polymers and glucose. This syrup, in which the fructose is in polymeric form, is useful as a specialty carbohydrate or it can be further treated to produce fructose syrups of greater than 50% fructose content. About half of the glucose in the intermediate syrup can be isomerized to fructose by means of a glucose isomerase enzyme. Subsequent hydrolysis of this reaction mixture cleaves the fructose polymers to fructose, thereby producing a high fructose syrup containing a major amount of fructose and minor amounts of glucose. The present invention is an improvement in this process.

SUMMARY OF THE INVENTION

In accordance with the present invention, there is provided an improved process for the production of fructose polymers from sucrose. The process involves contacting a sucrose-containing substrate with a mixture of a fructosyl transferase enzyme and a glucose isomerase enzyme preparation. The reaction product is a syrup which contains fructose polymers plus glucose and fructose. This syrup is useful as a specialty carbohydrate for sweetener and other applications. It may also be hydrolyzed to yield a syrup whose principal sugar is fructose. The fructose content of the sugars in these syrups is generally higher than 60% (by weight) and ranges up to about 75% and even higher, depending upon the composition of the sucrose substrate and the reaction conditions employed.

This simple process is surprisingly effective in producing high fructose syrups. The concurrent action of fructosyl transferase and glucose isomerase enzymes on sucrose gives fructose polymers with a substantially higher average percentage of fructose than those obtained by the sequential reaction of the same enzymes. Hydrolysis of the fructose polymers gives a high-fructose syrup which contains up to 15% more fructose than do the syrups obtained by hydrolysis of fructose polymers obtained by the sequential enzyme reactions of the prior art.

DETAILED DESCRIPTION OF THE INVENTION

For the purpose of this specification, the following definitions are provided for the various terms used herein:

1. Glucose and Dextrose

The terms "glucose" and "dextrose" are employed interchangeably in this application to embrace this monosaccharide in any form, in solution or dry.

2. Fructose and Levulose

The terms "fructose" and "levulose" are generally employed interchangeably in the art to refer to the isomer of dextrose that is sweeter than dextrose. Fructose is found in honey and in invert sugar, along with dextrose, and is valuable because of its sweetness. The terms levulose and fructose will be used interchangeably in this specification to refer to this monosaccharide in any form, in solution or dry.

3. High Fructose Syrup

This term as used herein refers to any syrup which contains more than 50% fructose by weight on a dry solids basis. It should be noted that commercial 42% fructose-bearing syrup is generally referred to as high fructose corn syrup, but is not intended to be included in the term as used herein.

4. Sucrose

The term "sucrose" refers to this disaccharide in refined or raw form, in solution or dry, from any sucrose raw material source, e.g., sugar cane or sugar beets. In the practice of this invention, the sucrose starting material is typically employed in aqueous medium.

5. Sucrose-Containing Substrate

The term "sucrose-containing substrate" is used herein to refer to any substrate whose sucrose content is at least 25% by weight of the sugars present. It includes molasses, turbinadoes, meladura, mixtures of sucrose and invert sugars, mixtures of sucrose and fructose-bearing syrup as well as purified sucrose.

6. Polysaccharide

The term "polysaccharide" is used herein to refer to any saccharide made up of two or more monosaccharide units.

7. Fructose Polymer

The term "fructose polymer" is used herein to refer to any polysaccharide in which the preponderence of monosaccharide units are fructose units.

8. Enzyme Preparation

The term "enzyme preparation" is used herein to refer to any composition of matter that exhibits the desired enzymatic activity. The term is used to refer, for example, to live whole cells, dry cells, cell extracts, refined and concentrated preparations derived from the cells and from culture liquors. The enzyme of the fructose polymers of this invention then gives a syrup with sugars containing up to 15% more fructose than that obtained by hydrolysis of fructose polymers obtained by the former method.

9. Transfructosylation

This term as used herein refers to the transfer of a fructosyl group from a donor, e.g., sucrose, to an acceptor, e.g., polysaccharide.

10. Fructosyl Transferase Enzyme

As used herein, this term refers to any enzyme that catalyzes transfructosylation and includes the enzyme preparation derived from *Pullularia pullulans*, ATCC No. 9348 (synonymous with *Aureobasidium pullulans*). In its preferred embodiments, the fructosyl transferase enzyme preparation of this invention contains the fructosyl transferase enzyme in a purified form, that is, separated from the fermentation culture medium in which it was produced.

11. Fructosyl Transferase Unit

As used herein, one fructosyl transferase unit is defined as the amount of enzyme activity required to produce one micromole of reducing sugar, calculated as glucose, per minute under the following conditions: (a) pH 5.5, (b) temperature 55° C., and (c) substrate concentration at 60 g food-grade sucrose per 100 ml of an aqueous reaction mixture.

Reducing sugar (calculated as glucose) is determined using a "Technicon Autoanalyzer II" (Technicon, Inc., Tarrytown, New York). Analysis is carried out by a conventional alkaline ferricyanide method, *Analytical Biochemistry* 45, No. 2, pp. 517–524 (1972), adapted for use in the "Autoanalyzer II". Unless otherwise designated, enzyme activity determinations are performed by continual monitoring of a reaction mixture consisting of the following composition:

7.5 ml of 80% (w/v) aqueous food-grade sucrose solution.

2.3 ml 0.1 M citrate buffer pH 5.5.

0.2 ml enzyme sample containing that amount of fructosyl transferase enzyme which will produce from 5–25 micrograms of reducing sugar (calculated as glucose) per minute per ml of reaction mixture.

12. Glucose Isomerase Enzyme

Any enzyme preparation that isomerizes dextrose to levulose is referred to herein as a glucose isomerase enzyme. These enzymes are well known in the art and have been referred to as dextrose isomerase, xylose isomerase and glucose isomerase. Such enzymes can be derived from a variety of suitable microorganisms. Sources, purification, definition of units and methods of analysis of glucose isomerase enzymes are given in U.S. Pat. No. 4,077,842, which is incorporated herein by reference in its entirety.

13. High Pressure Liquid Chromatographic Assay

This term as used herein defines a procedure whereby the syrups of the invention are analyzed using high pressure liquid chromatography in accordance with the following technique. Components are chromatographed by elution with water from a cation-exchange resin in the calcium form. Eluted components are detected by means of a differential refractometer. All carbohydrates are quantitated using an electronic integrator. The general procedure is that given in "Analysis of Carbohydrate Mixtures by Liquid Chromatography", *Am. Soc. Brew. Chem. Proc.*, 1973, pp. 43–46. The resin used is AMINEX 50W-X4 (20–30μ) in the calcium form, Bio-Rad Laboratories, Richmond, California.

The sucrose-containing substrate used in this invention may be a solution of either refined or raw sucrose. The substrate may also be a mixture of sucrose and varying amounts of other sugars wherein the sucrose content is at least 25% and preferably at least about 50% by weight of the sugars present. Preferred substrates are commercial sources of sucrose such as molasses of varying degrees of purity or mixtures of sucrose with invert sugar. Other useful substrates include meladura, turbinadoes and mixtures of sucrose and fructose-bearing syrups. It is usually a question of economics as to which sucrose source is used. This will depend on the step or steps in the process where purification is most economically achieved.

The fructosyl transferase enzyme preparations preferred for use in this invention may be any enzyme preparations capable of transferring the fructose moiety of sucrose to another molecule of sucrose or to other sugar molecules so that the products are polysaccharides comprising from 2 to about 10 fructosyl units per molecule. Many such enzyme preparations are known. Excellent results have been obtained using the fructosyl transferase enzyme preparations derived from *Pullularia pullulans* such as NRRL No. 3937; ATCC No. 9348; ATCC No. 12535; NRRL No. 1673; NRRL No. Y 2311; NRRL No. YB 3892; ATCC No. 15223; and NRRL No. YB 3861. A procedure for the preparation of the fructosyl transferase enzyme from *Pullularia pullulans* is given in British patent specification No. 2,000,144, which is incorporated herein by reference in its entirety. An additional method for its preparation is given in Example 1.

The sucrose-containing substrate is treated concurrently with a fructosyl transferase enzyme preparation and a glucose isomerase enzyme preparation to carry out the process of this invention. The amount of fructosyl transferase enzyme used may vary widely. Practical rates of reaction are observed when from 10 to 30 fructosyl transferase enzyme units are used per gram of sucrose in the substrate. Even higher rates of reaction are obtained by the use of larger amounts of the enzyme. The amount of glucose isomerase enzyme may also vary widely. Practical rates of reaction are observed when from 10 to 20 glucose isomerase enzyme units are used per gram of sucrose in the substrate.

The processes of this invention are carried out using aqueous solutions of the substrate. Substrate concentrations from as low as about 10% (w/v) may be employed. However, it is preferred to use as concentrated solutions as practical, preferably ranging from about 50% (w/v) up to saturation, so that there will be less need to evaporate water from the final product.

The reactions are carried out at temperatures ranging from room temperature up to temperatures just below those where rapid inactivation of the enzymes occur. A preferred temperature range for the reaction is from 50°–60° C. The pH of the reaction mixture may be varied depending on the pH optima of the particular enzymes used. It is convenient to use a pH range of from about 5.5 to about 7.0 with a preferred range of from about 6.3 to about 6.7 when the fructosyl transferase enzyme is that obtained from *Pullularia pullulans* ATCC No. 9348 and the glucose isomerase enzyme is that produced by *Streptomyces olivochromogenes*. It is also preferred to conduct the reactions in the presence of 0.005 M $Mg^{++}$.

When the process of this invention is carried out at a temperature of about 55° C., it has reached a practical degree of completion in about 24 hours. The enzymes present may be inactivated by heating the reaction mixture to about 100° C. for from 10 to 15 minutes. If desired, the enzymes can be removed from the reaction mixture either before or after heat inactivation by means of ultrafiltration through a filter of suitable size to remove such material.

The process of this invention may be carried out in either a batchwise or continuous mode. The continuous reaction may be carried out by circulating the reaction mixture through an ultrafiltration apparatus whereby the product is continually removed in the permeate from the ultrafilter and the enzymes are retained in the retentate from the ultrafilter. Fresh substrate and fresh enzymes as needed to replace those which have become inactivated are added to the reaction mixture at the same rate in which the permeate is removed from the ultrafilter.

If high fructose syrup is desired as a product, the fructose polymers of this invention may be hydrolyzed either before or after they are separated from the glucose present. Separation from the glucose may be accomplished by known chromatographic or membrane separation methods. Hydrolyzing agents and conditions of hydrolysis of the fructose polymers must be chosen so that the fructose is not destroyed. The reaction may be catalyzed by an acid or an acidic resin. Alternatively, the hydrolysis may be accomplished by means of enzymes such as those contained in commercially available invertase enzyme preparations.

The following examples further describe the embodiments of this invention. All parts are by weight and all percentages are weight by volume (w/v) unless expressly stated as to be otherwise.

EXAMPLE 1

Production of Fructosyl Transferase Enzyme

A. The Fermentation Procedure Used to Produce the Enzyme

The medium used for inoculum development and fermentation to produce the enzyme was as follows:
0.5% Dibasic Potassium Phosphate
0.1% Sodium Chloride
0.02% Magnesium Sulfate-Heptahydrate
0.06% Ammonium Sulfate
0.3% Yeast Extract (Difco Labs. Inc., Detroit, Michigan)
6.0% Sucrose (Food Grade)
pH of medium adjusted to 6.8

A first-stage inoculum was prepared as follows. The seed flasks, 500-ml Erlenmeyers containing 100 ml of sterile medium, were inoculated from a slant culture of the black yeast, *Pullularia pullulans*. The particular strain of the yeast employed is designated in the catalogue of the American Type Culture Collection (Rockville, Md.) as ATCC No. 9348. The seed flasks, after development on a reciprocal shaker for 48 hours at 31° C., were used to prepare a second-stage inoculum. This was accomplished by placing 0.25-ml portions of the first-stage inoculum in 25 ml of medium in 250-ml Erlenmeyer flasks. The second-stage inoculum was developed on a reciprocal shaker for 24 hours at 31° C. The entire contents of one flask was used to inoculate a 7.5-liter fermentor containing 5 liters of the medium. The medium was identical with that used for the seed flasks except that the sucrose was at a 12% concentration rather than a 6% concentration, and 0.04% of polypropylene glycol, mol. wt. 2000, antifoam agent was added. The fermentations were carried out at 32° C., with an agitator speed of 500 rpm and with 4 liters of air per minute passing through the mixture. Fermentation was conducted for a total of 65 hours.

B. Recovery of the Enzyme from the Cells

The pH of the fermentor broth was adjusted to 5.5 with 4 N NaOH solution before it was run through a Sharples continuous centrifuge to separate the cells and cellular debris from the supernatant. The wet cells were placed in a 1-liter Erlenmeyer flask with 2 volumes of water. After the addition of 1% toluene and a small amount of Triton X-100 (an alkyl phenoxy polyethoxy ethanol, non-ionic detergent, manufactured by the Rohm & Haas Corp., Philadelphia, Pa.), the flask was shaken for 1 hour on a reciprocal shaker to suspend the cells. The flask was then left at room temperature for 3 days with occasional hand mixing. The mixture was filtered through a filter precoated with diatomaceous earth, and the cell cake was washed with water. The filtrate was then concentrated by ultrafiltration through a Pellican Cassette System, manufactured by the Millipore Corp., Bedford, Mass., fitted with a cassette which retains material of greater than 10,000 molecular weight. During the concentration, the retentate was passed through reticulated foam before being returned to the ultrafiltration unit. The retentate was freeze-dried in a lyophilizer, ground in a mortar and pestle, washed with ethanol, and again lyophilized. The material from 6 such runs weighed a total of 39.9 g and showed an enzyme activity of 18,976 fructosyl transferase units per gram.

EXAMPLE 2

Preparation of Fructose Polymer Syrup and Glucose by the Concurrent Action of Fructosyl Transferase and Glucose Isomerase Enzymes on Sucrose Food-grade sucrose, 250 g was dissolved in 250 ml of water and magnesium chloride was added to a concentration of 0.005 M. The pH was adjusted to 6.5 and maintained at this value by the addition of 0.5 N sodium hydroxide solution was needed. To the sucrose solution was added 7500 units of fructosyl transferase enzyme preparation, obtained as in Example 1, and 5000 units of glucose isomerase enzyme preparation, obtained as described by Cory, U.S. Pat. No. 4,077,842. After the mixture had been stirred at 55° C. for 24 hours, the enzyme reaction was stopped by placing the material in a boiling water bath for 10 minutes. The resulting syrup was then analyzed by high pressure liquid chromatography. The results of two different runs using different batches of enzymes are given in Table I.

A portion of the syrup was diluted with water to give a 10% (w/v) solution. This was then hydrolyzed with invertase (Pfanstiehl Laboratories, Waukegan, Illinois) using 0.1 ml of invertase per 10 ml of solution. The solution was covered with a few drops of toluene to inhibit microbial growth and incubated at 32° C. for 48 hours. Carbohydrate content of the resulting syrup, as determined by high pressure liquid chromatography, is also reported in Table I.

The identity of the carbohydrate fractions separated quantitatively by the high pressure liquid chromatographic assay was determined in the following manner. Elution times of fructose, glucose and sucrose were determined by reference to elution times using known samples of pure crystalline sugars. Inulobiose, inulotriose, 1-kestose and nystose were all separated from the fructose polymer syrup mixtures by preparative high pressure liquid chromatography. The structures of the sugars so isolated were determined by $^{13}C$ NMR spectroscopy. The elution times of these sugars were used as references for their quantitative determination in mixtures. The positions of the quantitative elution peaks of the higher members of the inulobiose and 1-kestose series were determined by a graphical extrapolation technique.

COMPARATIVE TEST 1

(Prior Art Process)

Preparation of Fructose Polymer Syrups and Glucose by the Sequential Action of Fructosyl Transferase and Glucose Isomerase Enzymes on Sucrose A sucrose solution containing 0.005 M magnesium chloride was prepared as in Example 2. The pH was adjusted and maintained at 5.5 by the addition of 0.5 N sodium hydroxide solution as needed. Fructosyl transferase enzyme prepared as in Example 1 was added at a dosage of 30 units per gram of sucrose and the mixture was maintained at 55° C. for 24 hours with stirring. The fructosyl transferase enzyme was inactivated by heating the mixture in a boiling water bath for 15 minutes before the syrup was cooled to 55° C. and the pH adjusted to 7.0. To this solution was then added 20 units of glucose isomerase enzyme per gram of sucrose and the pH was maintained at 7.0 by the addition of 0.5 N sodium hydroxide solution as needed. After 24 hours at 55° C., the product was again heated to inactivate the glucose isomerase enzyme and the syrup was analyzed by high pressure liquid chromatography. Analysis of the product is given in Table I. A sample of the syrup was treated with invertase enzyme preparation as in Example 2 and the resulting high fructose syrup was analyzed by high pressure liquid chromatography. These results are also given in Table I.

The surprising synergistic action when the two enzymes are used together is shown by these results. The fructose polymer syrups produced contain much larger amounts of inulobiose ($F_2$), inulotriose ($F_3$) and higher members of the inulobiose series than do the syrups obtained by the sequential enzyme reactions of the prior art. In addition, hydrolysis of these fructose polymers yields a high fructose syrup containing a much higher percentage of fructose than that obtained by the former process (Comparative Test 1). Furthermore, these results are obtained in one-half the time of the prior process without the use of any additional enzyme and without the need to adjust the pH after 24 hours as was required when using sequential enzymatic reactions.

TABLE I

COMPOSITION OF SYRUPS PREPARED BY CONCURRENT AND SEQUENTIAL REACTIONS OF FRUCTOSYL TRANSFERASE AND GLUCOSE ISOMERASE WITH SUCROSE

| Carbohydrate[a] | Composition, % by Weight | | |
|---|---|---|---|
| | Example 2[b] | | Comparative |
| | Run 1 | Run 2 | Test 1[c] |
| $K_6$ | 2.5 | 3.2 | 4.6 |
| $K_5$ | 11.9 | 12.9 | 15.1 |
| $K_4$ | 18.8 | 19.7 | 20.5 |
| $K_3$ | 9.7 | 9.7 | 12.6 |
| $F_6$ | 1.8 | 1.5 | 0.4 |
| $F_5$ | 0.5 | 0.2 | 0.2 |
| S | 3.0 | 5.8[d] | 8.9[d] |
| $F_4$ | 3.0 | — | — |
| $F_3$ | 4.8 | 3.6 | 0.6 |
| G | 17.2 | 17.3 | 17.4 |
| $F_2$ | 9.3 | 7.6 | 1.1 |
| F | 17.1 | 18.2 | 18.3 |
| Composition After Hydrolysis With Invertase | | | |
| F | 72.1 | 69.8 | 65.0 |

TABLE I-continued

COMPOSITION OF SYRUPS PREPARED BY CONCURRENT AND SEQUENTIAL REACTIONS OF FRUCTOSYL TRANSFERASE AND GLUCOSE ISOMERASE WITH SUCROSE

| Carbohydrate[a] | Composition, % by Weight | | |
|---|---|---|---|
| | Example 2[b] | | Comparative |
| | Run 1 | Run 2 | Test 1[c] |
| G | 27.9 | 30.1 | 34.8 |

[a]The carbohydrates are listed in the order of their elution. F = fructose; $F_2$, $F_3$, etc. = inulobiose, inulotriose and higher members of the inulobiose series; S = sucrose; G = glucose; $K_3$ = 1-kestose; $K_4$ = nystose; $K_5$, etc. = higher members of the 1-kestose series.
[b]Fructosyl transferase and glucose isomerase used concurrently.
[c]Fructosyl transferase and glucose isomerase used sequentially.
[d]These values include both sucrose and $F_4$.

EXAMPLE 3

Preparation of Fructose Polymer Syrups by the Concurrent Action of Fructosyl Transferase with Varying Amounts of Glucose Isomerase Enzyme on Sucrose The general procedure of Example 2 was followed using 30 units of fructosyl transferase enzyme per gram of sucrose. Five runs were made using 5, 10, 15, 20 and 30 units of glucose isomerase per gram of sucrose, respectively Analyses of the resulting syrups before and after they were hydrolyzed with invertase are reported in Table II.

The results in Table II show that the percentage of fructose in the high fructose syrup obtained by the reaction of fructosyl transferase and glucose isomerase enzymes on sucrose increases with the amount of glucose isomerase enzyme employed. However, only small increases in the percentage of fructose are obtained when more than 15 to 20 units of glucose isomerase per gram of sucrose is employed. These experiments further show the ease of preparation of high fructose syrup with a relatively high percentage of fructose by the method of this invention.

TABLE II

COMPOSITION OF SYRUPS PREPARED BY THE CONCURRENT REACTION OF FRUCTOSYL TRANSFERASE AND VARYING AMOUNTS OF GLUCOSE ISOMERASE WITH SUCROSE

| Carbohydrate[a] | Compositon, % by Weight Run No.[b] | | | | |
|---|---|---|---|---|---|
| | 1 (5) | 2 (10) | 3 (15) | 4 (20) | 5 (30) |
| $K_6$ | 2.9 | 2.7 | 2.6 | 2.5 | 2.8 |
| $K_5$ | 12.3 | 12.4 | 12.1 | 11.9 | 12.2 |
| $K_4$ | 20.2 | 19.6 | 18.7 | 18.8 | 18.7 |
| $K_3$ | 11.3 | 9.6 | 9.7 | 9.7 | 9.5 |
| $F_6$ | — | 1.4 | 1.6 | 1.8 | 1.7 |
| $F_5$ | — | 0.3 | 0.4 | 0.5 | 0.4 |
| S | 6.3 | 3.0 | 2.9 | 3.0 | 2.7 |
| $F_4$ | — | 2.7 | 3.0 | 3.0 | 3.2 |
| $F_3$ | — | 4.4 | 4.7 | 4.8 | 5.2 |
| G | 23.7 | 18.7 | 17.7 | 17.2 | 16.5 |
| $F_2$ | 7.5 | 9.0 | 9.5 | 9.3 | 9.9 |
| F | 14.9 | 15.8 | 16.5 | 17.1 | 16.7 |
| Composition After Hydrolysis With Invertase | | | | | |
| F | 67.6 | 70.3 | 71.7 | 72.1 | 73.2 |
| G | 32.3 | 29.7 | 28.3 | 27.9 | 26.7 |

[a]Carbohydrate symbols have the same meaning as those in Table I.
[b]Number in parenthesis after the run number are the units of glucose isomerase enzyme per gram of sucrose. All runs used 30 units of fructosyl transferase per gram of sucrose.

EXAMPLE 4

Preparation of Fructose Polymer Syrups by the Concurrent Action of Varying Amounts of Fructosyl Transferase Plus Glucose Isomerase Enzymes on Sucrose The general procedure of Example 2 was followed using 20 units of glucose isomerase enzyme per gram of sucrose and varying amounts of fructosyl transferase enzyme in three different runs (30, 60 and 90 units per gram of sucrose, respectively). Analyses of the resulting syrups before and after hydrolysis with invertase are given in Table III.

The results given in Table III show that increasing the amount of fructosyl transferase enzyme used in the process of the present invention increases the percentage of fructose in the high fructose syrups formed. High fructose syrups containing greater than 75% fructose are readily obtained by this method.

TABLE III

COMPOSITION OF SYRUPS PREPARED BY CONCURRENT REACTION OF VARYING AMOUNTS OF FRUCTOSYL TRANSFERASE PLUS GLUCOSE ISOMERASE WITH SUCROSE

| Carbohydrate[a] | Composition, % by Weight Run No.[b] | | |
|---|---|---|---|
| | 1 (30) | 2 (60) | 3 (90) |
| $K_6$ | 2.6 | 4.2 | 4.6 |
| $K_5$ | 11.7 | 10.5 | 8.5 |
| $K_4$ | 18.5 | 11.4 | 7.5 |
| $K_3$ | 10.2 | 8.3 | 7.6 |
| $F_6$ | 1.9 | 2.8 | 2.6 |
| $F_5$ | 0.6 | 1.0 | 0.9 |
| S | 3.2 | 1.9 | 1.4 |
| $F_4$ | 2.9 | 4.0 | 5.0 |
| $F_3$ | 4.9 | 6.8 | 6.8 |
| G | 14.6 | 16.0 | 17.2 |
| $F_2$ | 9.3 | 11.2 | 12.2 |
| F | 19.1 | 20.2 | 23.1 |
| Composition After Hydrolysis With Invertase | | | |
| F | 73.9 | 77.1 | 78.0 |
| G | 26.0 | 22.7 | 21.7 |

[a]Carbohydrate symbols have the same meaning as those in Table I.
[b]Numbers in parenthesis after the run number are the units of fructosyl transferase enzyme per gram of sucrose. All runs used 20 units of glucose isomerase per gram of sucrose.

EXAMPLE 5

Preparation of High Fructose Syrups by the Concurrent Action of Fructosyl Transferase and Glucose Isomerase Enzymes on Mixtures of Sucrose and Commercial Fructose-Bearing Syrup To a solution of 120 g of sucrose and 60 g, on a dry solids basis, of a commercial fructose-bearing syrup which contained 41.2% fructose, 52.5% glucose and 6.3% non-fructose-containing polysaccharides in 120 ml water was added magnesium chloride to give a concentration of 0.005 M. The pH was adjusted to 6.5 and maintained at this value by the addition of 0.5 N sodium hydroxide solution as needed. To the foregoing solution was then added 5400 units of fructosyl transferase enzyme preparation obtained as in Example 1 and 3600 units of glucose isomerase enzyme preparation, obtained as described by Cory, U.S. Pat. No. 4,077,842. After the mixture had been stirred at 55° C. for 24 hours, the enzyme reaction was stopped by placing the material on a boiling water bath for 10 minutes. The resulting syrup was then analyzed by high pressure liquid chromatography.

The procedure of this example was repeated three times using different relative amounts of fructose-bearing syrup and sucrose. The ratios of fructose-bearing syrup to sucrose on a dry solids basis were 1:1, 2:1 and 3:1, respectively, in the three subsequent runs. Results of the analyses of the products are given in Table IV.

The results given in Table IV show that the process of this invention gives a convenient method for converting commercial fructose-bearing syrup to a higher fructose syrup in which between 57 and 67% of the dry substance is fructose. These runs also show that the amount of fructose in the high fructose syrup prepared by this method increases as the proportion of sucrose in the mixture increases.

TABLE IV

COMPOSITION OF SYRUPS PREPARED BY CONCURRENT REACTION OF FRUCTOSYL TRANSFERASE AND GLUCOSE ISOMERASE WITH MIXTURES OF SUCROSE AND COMMERCIAL FRUCTOSE-BEARING SYRUP

| Carbohydrate[a] | Composition, % by Weight Run No.[b] | | | |
|---|---|---|---|---|
| | 1 (1:2) | 2 (1:1) | 3 (2:1) | 4 (3:1) |
| $K_5$ | 3.5 | 1.4 | 0.3 | 0.2 |
| $K_4$ | 10.4 | 5.9 | 2.4 | 1.2 |
| $K_3$ | 7.2 | 5.2 | 2.8 | 2.0 |
| $F_6$ | 1.7 | 1.3 | 0.9 | 0.6 |
| $F_5$ | 0.6 | 0.5 | 0.3 | 0.2 |
| S | 3.9 | 4.1 | 3.5 | 3.6 |
| $F_4$ | 4.2 | 4.4 | 4.0 | 3.7 |
| $F_3$ | 4.8 | 3.7 | 2.0 | 1.4 |
| G | 25.4 | 30.4 | 35.5 | 39.7 |
| $F_2$ | 11.7 | 12.6 | 11.2 | 9.2 |
| F | 26.3 | 30.2 | 36.7 | 38.0 |
| Composition After Hydrolysis With Invertase | | | | |
| F | 67.2 | 63.5 | 59.2 | 57.0 |
| G | 30.8 | 33.7 | 37.2 | 39.2 |

[a]Carbohydrate symbols have the same meaning as those in Table I.
[b]Numbers in parenthesis after the run number are the ratios of fructose syrup:sucrose on a dry substance basis. The commercial fructose syrup contained 41.2% fructose and 52.5% glucose on a dry substance basis.

EXAMPLE 6

Semicontinuous Production of Fructose Polymer Syrups

A 3.6-liter reactor was fitted with inlet and outlet tubes so that the reaction mixture could be continuously pumped from the reactor through an ultrafiltration apparatus with the retentate from the ultrafiltration apparatus being recycled back to the reactor. The ultrafiltration apparatus used was the Pellican Cassette System, manufactured by the Millipore Corp., Bedford, Mass., fitted with a cassette which retains material of greater than 10,000 molecular weight. A sucrose solution was prepared by dissolving sucrose in an equal weight of water. The reactor was charged with 1 liter of the sucrose solution, 64,800 units of fructosyl transferase enzyme prepared as in Example 1, and 32,400 units of glucose isomerase enzyme. The pH of the solution was adjusted to 6.5 and maintained at this pH throughout the reaction by addition of 0.5 N sodium hydroxide solution as needed. The mixture was agitated at 55° C. and circulated through the ultrafiltration apparatus. No permeate was removed from the ultrafiltration apparatus during the first 4 hours of reaction. The volume of the reaction mixture was increased by the addition of an additional 250 ml of sucrose solution every 15 minutes until a total of 2 additional liters of syrup had been added. Then 600 ml of sucrose syrup containing an additional 43,200 units of fructosyl transferase enzyme were added. After 4 hours of reaction, the product from the reactor was cycled through the ultrafiltration apparatus. A total of 1200 ml of permeate was collected and a corresponding 1200 ml of sucrose solution was added to the reactor. The fresh sucrose solution contained 1 unit of glucose isomerase and 5 units of fructosyl transferase enzyme per gram of sucrose. The reaction was continued for 170 hours with 1200 ml of permeate being removed every 4 hours and corresponding 1200 ml of sucrose solution being added every 4 hours. After 44 hours of reaction, the amount of fresh glucose isomerase enzyme added to the reactor was increased to 5 units per gram of fresh sucrose added. However, this did not change the composition of the product obtained. Samples of the permeate were hydrolyzed with invertase enzyme by the method described in Example 2 and the resulting high fructose syrups were analyzed by high pressure liquid chromatography with the following results:

| Composition, Time (hrs) | Fructose Syrup % by Weight | |
| --- | --- | --- |
| | Fructose | Glucose |
| 4 | 56.0 | 44.0 |
| 8 | 60.9 | 39.1 |
| 12 | 63.6 | 36.4 |
| 20 | 63.9 | 36.1 |
| 40 | 64.7 | 35.3 |
| 60 | 65.3 | 34.7 |
| 80 | 66.9 | 32.6 |
| 100 | 65.8 | 34.2 |
| 120 | 65.3 | 34.7 |
| 140 | 65.5 | 34.5 |
| 160 | 64.0 | 36.0 |

These results show that the process of this invention is capable of being carried out in a semicontinuous reaction to produce a high fructose syrup containing over 60% of fructose on a dry substance basis.

What is claimed is:

1. A process for the preparation of fructose polymers which comprises subjecting a sucrose-containing substrate to the concurrent action of effective amounts of fructosyl transferase and glucose isomerase enzyme preparations for a time and under conditions effective to form fructose polymers, glucose and fructose.

2. The process of claim 1 wherein the fructosyl transferase enzyme preparation is derived from *Pullularia pullulans*, ATCC No. 9348.

3. The process of claim 2 wherein the reaction is carried out at a temperature of about 50° C. to about 60° C. and at a pH of about 6.3 to about 6.7.

4. The process of claim 1 wherein the sucrose-containing substrate comprises sucrose and a fructose-bearing syrup.

5. The process of claim 1 wherein the reaction is carried out in a continuous mode.

6. A process for the preparation of a high fructose syrup which comprises subjecting a sucrose-containing substrate to the concurrent action of effective amounts of fructosyl transferase and glucose isomerase enzyme preparations for a time and under conditions effective to form fructose polymers, glucose and fructose, and hydrolyzing said fructose polymers to yield a syrup whose principal sugar is fructose.

7. The process of claim 6 wherein said fructosyl transferase enzyme preparation is derived from *Pullularia pullulans*, ATCC No. 9348.

8. The process of claim 7 wherein the reaction is carried out at a temperature of from about 50° C. to about 60° C. and at a pH of from about 6.3 to about 6.7.

9. The process of claim 6 wherein the sucrose-containing substrate comprises sucrose and a fructose-bearing syrup.

10. The process of claim 6 wherein the first step of the process is carried out as a continuous process.

11. The process of claim 6 wherein the fructose polymers are separated from glucose before hydrolyzing the fructose polymers.

12. The product obtained by the process of claim 1.

* * * * *